US006316498B1

(12) United States Patent
Nakazato et al.

(10) Patent No.: US 6,316,498 B1
(45) Date of Patent: Nov. 13, 2001

(54) FLUORINE-CONTAINING AMINO ACID DERIVATIVES

(75) Inventors: Atsuro Nakazato; Toshihito Kumagai; Kazunari Sakagami; Kazuyuki Tomisawa, all of Tokyo (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/601,131

(22) PCT Filed: Jan. 27, 1999

(86) PCT No.: PCT/JP99/00324

§ 371 Date: Jul. 27, 2000

§ 102(e) Date: Jul. 27, 2000

(87) PCT Pub. No.: WO99/38839

PCT Pub. Date: Aug. 5, 1999

(30) Foreign Application Priority Data

Jan. 28, 1998 (JP) .................................................. 10-015444

(51) Int. Cl.[7] .......................... C07C 69/74; C07C 61/12; A01N 37/00; A01N 37/12
(52) U.S. Cl. .......................... 514/510; 514/561; 562/501; 560/119
(58) Field of Search .................................... 562/501, 119; 514/510, 561

(56) References Cited

U.S. PATENT DOCUMENTS 5,750,566    5/1998    Monn et al. .......................... 514/510
5,958,960  * 9/1999    Massey et al. .

FOREIGN PATENT DOCUMENTS

| 0 696 577 A1 | 2/1996  | (EP) | ............................. | C07C/229/50 |
| 0 878 463 A1 | 11/1998 | (EP) | ............................. | C07C/229/50 |
| 8-188561     | 7/1996  | (JP) | ............................. | C07C/229/50 |
| 96/05175     | 2/1996  | (WO) | ............................. | C07D/235/02 |
| 98/51655     | 11/1998 | (WO) | ............................. | C07C/61/08  |

OTHER PUBLICATIONS

International Search Report.

* cited by examiner

Primary Examiner—Paul J. Killos
Assistant Examiner—Mahreen Chaudhry
(74) Attorney, Agent, or Firm—Sughrue, Mion, Zinn, Macpeak & Seas, PLLC

(57) ABSTRACT

Fluorine-containing amino acid derivatives represented general formula (I), pharmaceutically acceptable salts thereof or hydrates of the same, wherein $X^1$ represents hydrogen or fluorine; and $R^1$ and $R^2$ are the same or different and each represents hydrogen or lower $C_{1-10}$ alkyl. These compounds are useful as drugs, in particular, group 2 metabotropic glutamate receptor agonists for treating and preventing psychiatric disorders such as schizophrenia, anxiety and associated diseases, depression, bipolar disturbance and epilepsy, and neurological diseases such as drug addiction, cognition disorder, Alzheimer's disease, Huntington's chorea, Parkinson's disease, motility disturbance associating muscular stiffness, cerebral ischemia, cerebral insufficiency, spinal cord lesion and head disturbance.

8 Claims, No Drawings

FLUORINE-CONTAINING AMINO ACID DERIVATIVES

FIELD OF TECHNOLOGY

This invention relates to fluorine-containing amino acid derivatives that are useful as drugs; it relates to novel fluorine-containing amino acid derivatives that are useful for the treatment and prevention of psychiatric disorders such as, for example, schizophrenia, anxiety and associated diseases, neurological diseases such as depression, bipolar disorder and epilepsy, as well as drug dependence, cognitive disorders, Alzheimer's disease, Huntington's chorea, Parkinson's disease, movement impairment associated with muscular stiffness, cerebral ischemia, cerebral insufficiency, spinal cord lesions, and head trauma.

This specification is based on Japanese Patent Application, No. Hei 10-15444 [1998], the content of which is herein incorporated by reference, as part of this specification.

BACKGROUND TECHNOLOGY

In recent years, with the repeated cloning of glutamate receptor genes, it has become clear that there are surprisingly many subtypes of glutamate receptors. At present, glutamate receptors are broadly classified into two types: the "ionotropic type", in which the receptor has an ion channel structure, and the "metabotropic type", in which the receptor is coupled to G-proteins (Science, 258, 597–603, 1992). Ionotropic receptors are classified pharmacologically into three types: N-methyl-D-asparaginic acid (NMDA), α-amino-3-hydroxy-5-methyl isoxazole-4-propionate AMPA), and kynate (Science, 258, 597–603, 1992). Metabotropic receptors are classified into eight types, type 1 through type 8 (J. Neurosci., 13, 1372–1378, 1993; Neuropharmacol., 34, 1–26, 1995).

The metabotropic glutamate receptors are classified pharmacologically into three groups. Of these, group 2 (mGluR2/mGluR3) bind with adenylcyclase, and inhibit the accumulation of the Forskolin stimulation of cyclic adenosine monophosphate (cAMP) (Trends Pharmacol. Sci., 14, 13 (1993)), which suggests that compounds that act on group 2 metabotropic glutamate receptors should be useful for the treatment or prevention of acute and chronic psychiatric and neurological disorders. As a substance that acts on group 2 metabotropic glutamate receptors, (+)-(1S,2S,5R,6S)-2-aminobicyclo[3.1.0]hexane-2,6-dicarboxylic acid has been disclosed in Japanese Unexamined Patent Publication, No. Hei 8-188561 [1996].

Fluorine atoms tend to be strongly electron-attractive and to confer high fat solubility, and compounds into which fluorine atoms are introduced greatly change their physical properties. Thus introducing fluorine atoms might greatly affect the absorbability, metabolic stability, and pharmacological effects of a compound. But it is by no means easy to introduce fluorine atoms. In fact, Japanese Unexamined Patent Publication No. Hei 8-188561 [1996] does not even discuss the introduction of fluorine atoms into (+)-(1S,2S, 5R,6S)-2-aminobicyclo[3.1.0]hexane-2,6-dicarboxylic acid.

DISCLOSURE OF THE INVENTION

In view of the aforementioned present state of the prior art, the purpose of this invention is to provide drugs that are effective for the treatment and prevention of, for example, schizophrenia, anxiety and associated diseases, depression, bipolar disorder, epilepsy and other psychiatric disorders, as well as drug dependence, cognitive disorders, Alzheimer's disease, Huntington's chorea, Parkinson's disease, movement impairment associated with muscular stiffness, cerebral ischemia, cerebral insufficiency, spinal cord lesions, head trauma and other neurological diseases; especially oral drugs that can act on group 2 metabotropic glutamate receptors.

The inventors of this invention, having made a diligent study of fluorine-containing amino acid derivatives in which fluorine atoms are introduced into (+)-(1S, 2S, 5R, 6S)-2-aminobicyclo[3.1.0]hexane-2,6-dicarboxylic acid, have discovered novel fluorine-containing amino acid derivatives that when taken orally can affect group 2 metabotropic glutamate receptors.

That is, this invention consists of a 2-amino-3-fluorobicyclo[3.1.0]hexane-2,6-dicarboxylic acid derivative represented by formula [I]

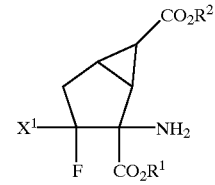

[where $X^1$ represents a hydrogen atom or fluorine atom, $R^1$ and $R^2$ are the same or different and each represents a hydrogen atom or an alkyl group of 1–10 carbon atoms], a pharmaceutically permissible salt thereof, or a hydrate thereof.

In this invention, the alkyl group of 1–10 carbon atoms means a straight-chain or branched-chain alkyl group, or a cycloalkyl group, where one can cite as a straight-chain or branched-chain alkyl group, for example, a methyl group, an ethyl group, a propyl group, an isopropyl group, a butyl group, an isobutyl group, a pentyl group, an isopentyl group, a 1-ethylpropyl group, a hexyl group, an isohexyl group, a 1-ethylbutyl group, a heptyl group, an isoheptyl group, an octyl group, a nonyl group, a decyl group, etc., and one can cite as a cycloalkyl group including an alkyl group that is substituted with a cycloalkyl group of 3–10 carbon atoms, for example, a cyclopropyl group, a cyclobutyl group, a cyclopropylmethyl group, a cyclopentyl group, a cyclobutylmethyl group, a cyclohexyl group, a cyclopentylmethyl group, a cyclohexylmethyl group, a cycloheptyl group, etc.

As a pharmaceutically permissible salt in this invention, one can cite, for example, a salt with an inorganic acid such as sulfuric acid, hydrochloric acid, phosphoric acid, etc., a salt with an organic acid such as acetic acid, oxalic acid, lactic acid, tartaric acid, fumaric acid, maleic acid, methanesulfonic acid, benzenesulfonic acid, etc., a salt with an amine such as trimethyl amine, methyl amine, etc., or a salt with a metal ion such as sodium ion, potassium ion, calcium ion, etc. The compounds of this invention may exist as various solvates, but from the standpoint of applicability as a drug, hydrates are preferable.

In a compound represented by formula [I], if $X^1$ is a hydrogen atom, five asymmetric carbon atoms are present in positions 1, 2, 3, 5, and 6. Therefore a compound of this invention in which $X^1$ is a hydrogen atom can exist as a mixture of two kinds of enantiomers such as optically active substances and racemic compounds, and a mixture of diastereomers. And if $X^1$ is a fluorine atom, four asymmetric carbon atoms are present in positions 1, 2, 5, and 6.

Therefore a compound of this invention in which $X^1$ is a fluorine atom can exist as a mixture of two kinds of enantiomers such as optically active substances and racemic compounds, and a mixture of diastereomers.

An $X^1$ that is desirable in the compounds represented by formula [I] is a hydrogen atom. And, if $X^1$ is a hydrogen atom, it is more desirable that the compounds represented in formula [I] have the following stereochemical configuration.

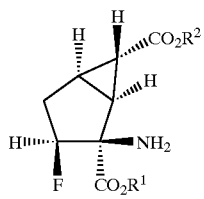

And if $X^1$, $R^1$ and $R^2$ are hydrogen atoms, then the optically active substance that is most desirable among the optical isomers of this compound has a positive optical rotation, and this absolute stereochemical arrangement has been determined to be 1S, 2S, 3S, 5R, 6S by x-ray single crystal structural analysis of 2-spiro-5'-hydantoin-3-fluorobicyclo[3.1.0]hexane-6-carboxylic acid (R)-(+)-1-phenylethylamine salt, which is a synthesis precursor of this compound.

On the other hand, if in formula [I] one or both of $R^1$ and $R^2$ represent something other than hydrogen, that is, the ester form will not have an effect on group 2 metabotropic glutamate receptors. But this ester form is hydrolyzed in vivo and is transformed into carboxylic acid, which does have an effect on group 2 metabotropic glutamate receptors. In this way, the ester forms of the compounds of this invention are very useful because they function as prodrugs.

The compounds of formula [I] can be manufactured according to the following reaction formulas. In the following reaction formulas, $R^1$, $R^2$ and $X^1$ are the same as above, $R^3$ and $R^4$ are the same or different and each represents a lower alkyl group of 1–10 carbon atoms, and Y represents a common protective group for an amino group (see Protective Groups in Organic Synthesis, by Theodora W. Greene and Peter G. M. Wuts).

First, as shown in the following reaction formula, one or two fluorine atoms are introduced in the prescribed position of ketone derivative (1), which is the starting substance.

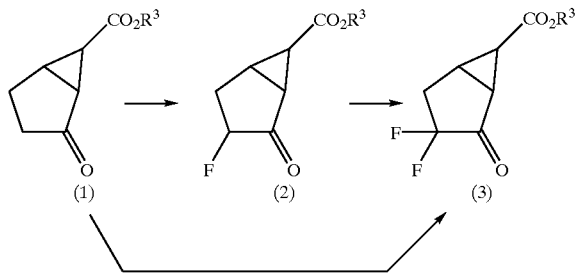

Monofluoride compound (2), which is a mixture of two kinds of enantiomers such as optically active substances and racemic compounds or a mixture of diastereomers, is obtained by temporarily making ketone derivative (1), which is a mixture of two kinds of enantiomers such as optically active substances and racemic compounds or a mixture of diastereomers, into an enol sylil ether derivative or enol ester derivative, then either reacting it with a fluorination reagent, or by directly reacting a fluorination reagent with ketone derivative (1). Difluoride compound (3), which is a mixture of two kinds of enantiomers such as optically active substances and racemic compounds or a mixture of diastereomers, is obtained by temporarily making monofluoride compound (2) into an enol sylil ether derivative, then reacting it with a fluorination reagent, or by directly reacting monofluoride compound (2) with a fluorination reagent, or by reacting 2 equivalents or more of a fluorination reagent with ketone derivative (1).

Here, the enol sylil ether derivative can be manufactured by reacting ketone derivative (1) with a silylation agent such as chlorotrimethylsilane and chloro t-butyldimethylsilane, in an inactive solvent such as ethers such as tetrahydrofuran and diethyl ether, hydrocarbons such as toluene and benzene, alcohols such as methanol and t-butanol, and N,N-dimethylformamide, in the presence of a base such as alkyl lithium such as n-butyl lithium and s-butyl lithium, metal amide such as lithium bis (trimethylsylil) amide, potassium bis(trimethylsilyl)amide and sodium amide, metal hydrides such as sodium hydride, and amine such as triethylamine. The reaction temperature is preferably no greater than 100° C., and more preferably from −78° C. to room temperature.

The enol ester derivative can be manufactured in the same way that the enol sylil ether derivative is manufactured, by replacing said silylation agent with an acid anhydride such as acetic anhydride, an acyl halide such as propionyl chloride, or a mixed acid anhydride prepared by treatment of a carboxylic acid such as acetic acid with an alkoxycarbonyl halide such as ethoxycarbonyl chloride.

As the fluorination reagent, one can use, for example, an N-fluoro-type fluorination agent such as N-fluoropyridinium triflate, N-fluoro-N-t-butylbenzenesulfonamide, N-fluorosaccharin sultam, N-fluorobis(benzenesulfone) imide, N-fluoro-o-benzenesulfone, etc., fluorine, an inorganic fluoride compound such as hydrogen fluoride and acidic potassium fluoride ($HKF_2$), $ClO_3F$, $CF_3COOF$, etc.

What is desirable as the mode for directly reacting the fluorination reagent, is to cause said fluorination reagent to react with ketone (1) in an inactive solvent such as ethers, for example tetrahydrofuran, diethyl ether, etc., hydrocarbons such as toluene and benzene, alcohols such as methanol and t-butanol, and N,N-dimethylformamide, under the presence of a base such as an alkyl lithium, for example n-butyl lithium, s-butyl lithium, etc., a metal amide such as lithium bis(trimethylsilyl)amide and sodium amide, metal hydrides such as sodium hydride, and an amide such as triethylamine at a reaction temperature preferably no greater than 100° C., and more preferably from −78° C. to room temperature.

As shown in the following reaction scheme, the mono- or di-fluoride compound (4) thus obtained, which is a mixture of two kinds of enantiomers such as optically active substances and racemic compounds or a mixture of diastereomers, can be made into fluorine-containing amino acid derivative (5), which is the compound according to this invention and is a mixture of two kinds of enantiomers such as optically active substances and racemic compounds or a mixture of diastereomers, by hydrolyzing amino cyanide derivatives or hydantoin derivatives, etc. obtained by Strecker amino acid synthesis (Ann., 75, 27 (1850); 91, 349 (1850)), the Bucherer-Bergs reaction (J. Prakt. Chem., 140, 69 (1934)), or a variation of these.

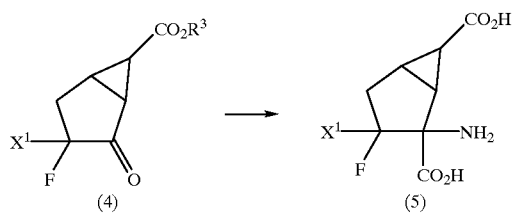

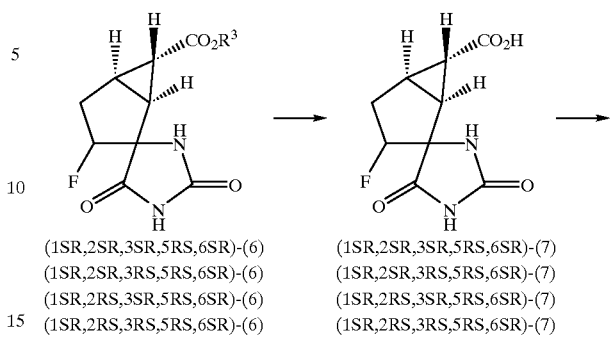

(1SR,2SR,3SR,5RS,6SR)-(6)  (1SR,2SR,3SR,5RS,6SR)-(7)
(1SR,2SR,3RS,5RS,6SR)-(6)  (1SR,2SR,3RS,5RS,6SR)-(7)
(1SR,2RS,3SR,5RS,6SR)-(6)  (1SR,2RS,3SR,5RS,6SR)-(7)
(1SR,2RS,3RS,5RS,6SR)-(6)  (1SR,2RS,3RS,5RS,6SR)-(7)

Specifically, mono- or di-fluoride compound (4) can be made into the hydantoin derivative that is a synthesis intermediate by reacting it with, for example, sodium cyanide or potassium cyanide, and ammonium carbonate in alcohols such as ethanol or a mixed solvent of alcohols and water, preferably for 1–2 days at 30–50° C. Said hydantoin derivative can be made into fluorine-containing amino acid derivative (5), which is a compound according to this invention, by further hydrolyzing it with a base such as sodium hydroxide or an acid such as hydrochloric acid and sulfuric acid in, for example, alcohols such as ethanol, ethers such as dioxane, ketones such as acetone.

As shown in the following formulas, the hydantoin derivatives represented by (1SR,5RS,6SR)-(6) obtained by the Bucherer-Bergs reaction of the monofluoride compound (see (2) above) in which one fluorine atom is introduced in the ketone derivative represented by (1SR,5RS,6SR)-(1) can be separated into the four diastereomers (1SR,2SR,3SR, 5RS,6SR), (1SR,2SR,3RS,5RS,6SR), (1SR,2RS,3SR,5RS, 6SR), (1SR,2RS,3RS,5RS,6SR) by a general technique such as, for example, column chromatography using silica gel, etc. or recrystallization, etc.

Moreover, these four diastereomers can be resolved into the eight enantiomers (8) (1S,2S,3S,5R,6S), (1R,2R,3R,5S, 6R), (1S,2S,3R,5R,6S), (1R,2R,3S,5S,6R), (1S,2R,3S,5R, 6S), (1R,2S,3R,5S,6R), (1S,2R,3R,5R,6S), (1R,2S,3S,5S, 6R) by hydrolyzing the ester position of each and making it into a carboxylic acid derivative represented by (7), then performing general resolution such as, for example, resolution using a basic chiral resolving agent. Then these enantiomers (8) can be made into eight optically active fluorine-containing amino acid derivatives (9) that are compounds according to this invention by hydrolyzing their hydantoin moiety.

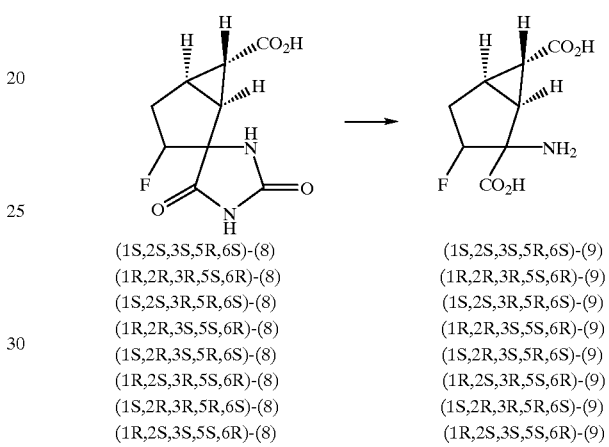

(1S,2S,3S,5R,6S)-(8)   (1S,2S,3S,5R,6S)-(9)
(1R,2R,3R,5S,6R)-(8)   (1R,2R,3R,5S,6R)-(9)
(1S,2S,3R,5R,6S)-(8)   (1S,2S,3R,5R,6S)-(9)
(1R,2R,3S,5S,6R)-(8)   (1R,2R,3S,5S,6R)-(9)
(1S,2R,3S,5R,6S)-(8)   (1S,2R,3S,5R,6S)-(9)
(1R,2S,3R,5S,6R)-(8)   (1R,2S,3R,5S,6R)-(9)
(1S,2R,3R,5R,6S)-(8)   (1S,2R,3R,5R,6S)-(9)
(1R,2S,3S,5S,6R)-(8)   (1R,2S,3S,5S,6R)-(9)

As the basic chiral resolving agent, one can use, for example, optically active amines such as (+) or (−)-1-phenylethylamine, (+) or (−)-2-amino-1-butanol, (+) or (−)-alaninol, brucine, cinchonidine, cinchonine, quinine, quinidine, dehydroabiethylamine, etc.

Meanwhile, the four optically active (1S,2S,5R,6S), (1R, 2R,5S,6R), (1S,2R,5R,6S), (1R,2S,5S,6R)-fluorine-containing amino acid derivatives (12) that contain two fluorine atoms and are one of the compounds according to this invention can be synthesized, as shown in the following formulas, by taking (1SR,5RS,6SR)-(1) as the starting material, performing, as in the above case, fluorination, hydantoinization, separation of diastereomers (10), generation of derivatives (11) by hydrolysis of the ester moiety, resolution, and hydrolysis of the hydantoin moiety.

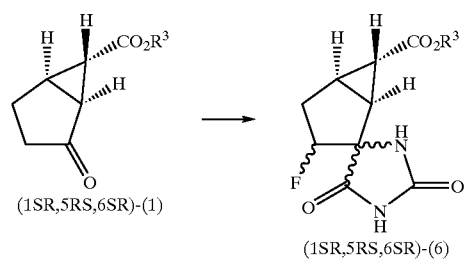

(1SR,5RS,6SR)-(1)   (1SR,5RS,6SR)-(6)

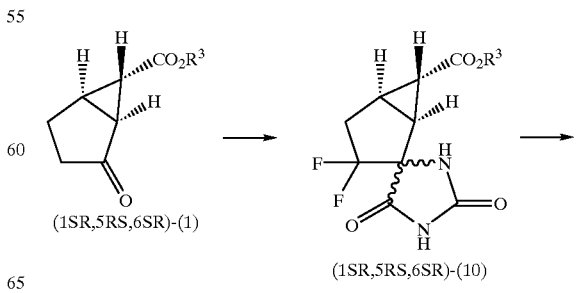

(1SR,5RS,6SR)-(1)   (1SR,5RS,6SR)-(10)

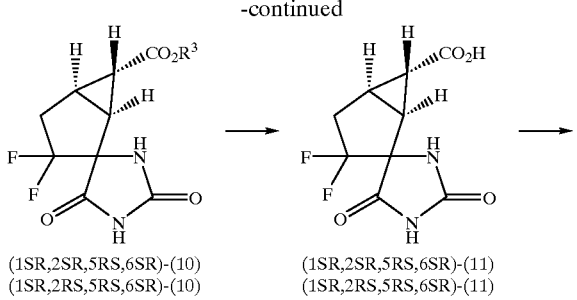

(1SR,2SR,5RS,6SR)-(10)
(1SR,2RS,5RS,6SR)-(10)

(1SR,2SR,5RS,6SR)-(11)
(1SR,2RS,5RS,6SR)-(11)

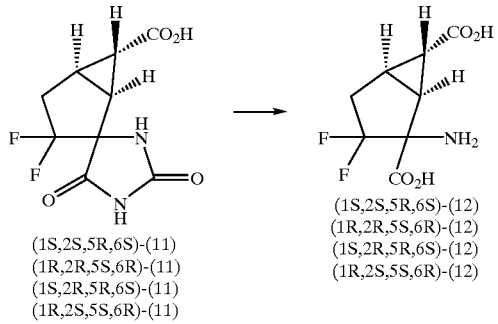

(1S,2S,5R,6S)-(11)
(1R,2R,5S,6R)-(11)
(1S,2R,5R,6S)-(11)
(1R,2S,5S,6R)-(11)

(1S,2S,5R,6S)-(12)
(1R,2R,5S,6R)-(12)
(1S,2R,5R,6S)-(12)
(1R,2S,5S,6R)-(12)

Also, as shown in the following formulas, the monofluoride compound represented by (1SR,5RS,6SR)-(2), which has one fluorine atom, can be made into the four optically active ketocarboxylic acids (13) of (1S,3S,5R,6S), (1R,3R,5S,6R), (1S,3R,5R,6S), (1R,3S,5S,6R) by separation of the diastereomers by general techniques, hydrolysis of the ester moiety, and resolution.

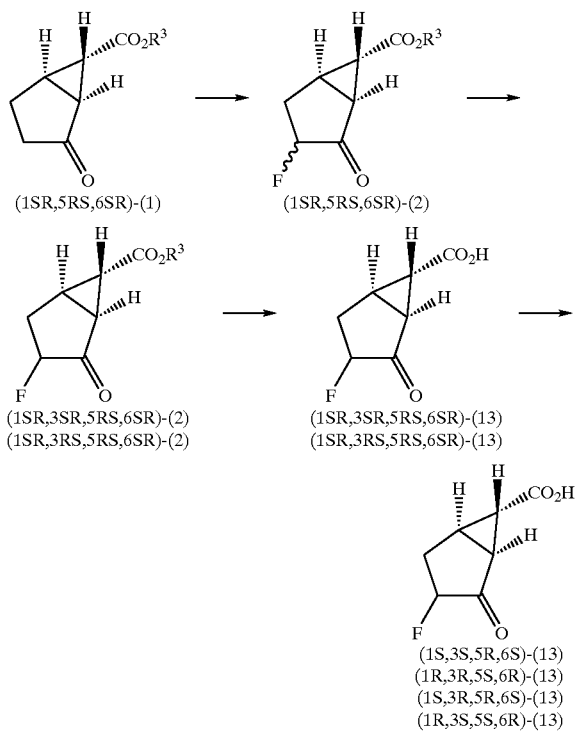

(1SR,5RS,6SR)-(1)

(1SR,5RS,6SR)-(2)

(1SR,3SR,5RS,6SR)-(2)
(1SR,3RS,5RS,6SR)-(2)

(1SR,3SR,5RS,6SR)-(13)
(1SR,3RS,5RS,6SR)-(13)

(1S,3S,5R,6S)-(13)
(1R,3R,5S,6R)-(13)
(1S,3R,5R,6S)-(13)
(1R,3S,5S,6R)-(13)

Therefore, the fluorine-containing amino acid derivatives that are the optically active compounds according to this invention can be manufactured by carrying out for the four optically active ketocarboxylic acids (13) the same operation as in the case of the synthesis of the compounds represented by (5), either directly or after their esterification, and further separating the diastereomers.

And, as shown in the following formulas, the two optically active ketocarboxylic acids (14) (1S,5R,6S) and (1R,5S,6R) that have two fluorine atoms can be obtained from the ketone derivatives represented by (1SR,5RS,6SR)-(3) having two fluorine atoms by the same operation as in the case of the synthesis of the compounds represented by (13), that is, by ester hydrolysis and resolution.

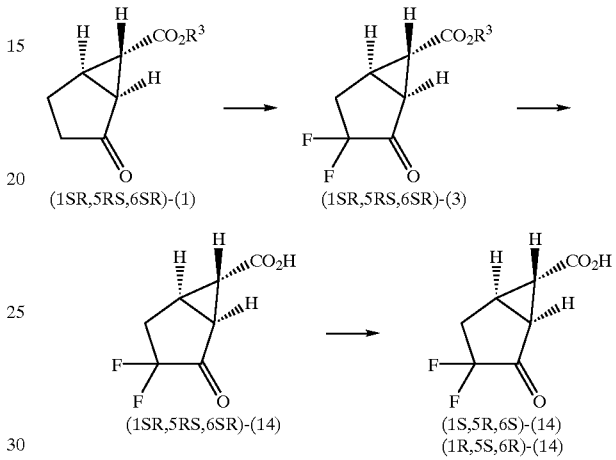

(1SR,5RS,6SR)-(1)

(1SR,5RS,6SR)-(3)

(1SR,5RS,6SR)-(14)

(1S,5R,6S)-(14)
(1R,5S,6R)-(14)

Therefore, the fluorine-containing amino acid derivatives that are the optically active compounds according to this invention can be manufactured by carrying out for the two optically active ketocarboxylic acids (14) the same operation as in the case of the synthesis of the compounds represented by (5), either directly or after their esterification, and further separating the diastereomers.

Further, as shown in the following formulas, the fluorine-containing amino acid esters that are the compounds according to this invention represented by (15) can be derived from the fluorine-containing amino acids that are compounds according to this invention and exist as a mixture of two kinds of enantiomers such as the optically active substances and racemic compounds or a mixture of diastereomers represented by formula (6), by protecting the amino group by the protective group represented by Y, then carrying out esterification by a general method using an alkyl halide represented by $R^3$—$X^2$ or $R^4$—$X^2$, alternatively an alcohol represented by $R^3$—OH or $R^4$—OH, and removing the protective group of the amino group.

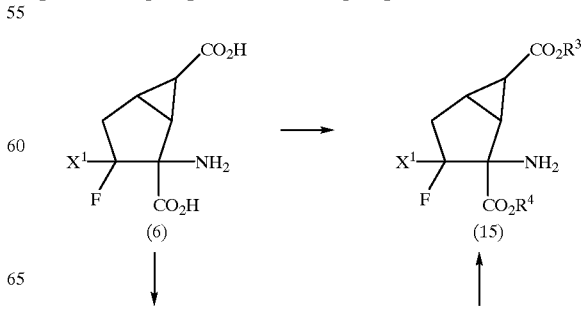

(6)

(15)

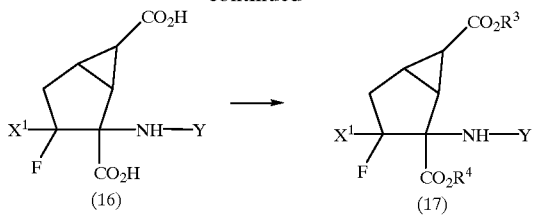

Here, protection of the amino group, esterification and removal of the protection of the amino group can be done by a general method such as that described in Protective Groups in Organic Synthesis, by Theodora W. Greene and Peter G. M. Wuts, which is herein incorporated by reference.

Moreover, the fluorine-containing amino acid esters represented by formula (15) or the diastereomers of the N-protected fluorine-containing amino acid esters represented by formula (17) can be separated by a general method such as column chromatography using silica gel or recrystallization. And, the diastereomers of formula (15) can be resolved into enantiomers by a general method such as resolution using an acidic chiral resolving agent.

Here, as the acidic chiral resolving agent, one can use optically active organic acids such as (+) or (−)-di-p-toluoyl tartaric acid, (+) or (−)-dibenzoyl tartaric acid, (+) or (−)-tartaric acid, (+) or (−)-mandelic acid, (+) or (−)-camphoric acid, or (+) or (−)-camphorsulfonic acid.

The compounds according to this invention can be made into pharmaceutical preparations by combining them with one or more pharmaceutically permissible carriers, vehicles, or diluents. Examples of said carriers, vehicles and diluents include water, lactose, dextrose, fructose, sucrose, sorbitol, mannitol, polyethylene glycol, propylene glycol, starch, gum, gelatin, arginate, calcium silicate, calcium phosphate, cellulose, water syrup, methyl cellulose, polyvinyl pyrrolidone, alkyl parahydroxy benzoate, talc, magnesium stearate, stearic acid, glycerin, and oils such as sesame oil, olive oil and soybean oil.

The compounds according to this invention, after being mixed with these carriers, vehicles or diluents, and, if necessary, with additives such as generally used fillers, binders, disintegrants, pH regulators and solvents, can, by means of usual drug-making technology, be prepared as oral or non-oral drugs, especially as drugs that act on group 2 metabotropic glutamate receptors, in such forms as tablets, pills, capsules, granules, powders, liquids, emulsions, suspensions, ointments, injections and skin plasters. The compounds according to this invention can be administered orally or non-orally to an adult patient in a quantity of 0.01–500 mg once or several times per day, but for ease of use and pharmacological efficacy, oral administration is preferred. This dosage can be increased or decreased as appropriate in consideration of the type of disease being treated and the patient's age, weight and symptoms.

PREFERRED EMBODIMENTS OF THE INVENTION

In the following, we describe this invention specifically by presenting working examples and experimental examples. However, it goes without saying that this invention is not thereby limited to these examples.

EXAMPLE 1

Syntheses of (1SR,3RS,5RS,6SR)ethyl 3-fluoro-2-oxobicyclo[3.1.0]hexane-6-carboxylate and (1SR, 3SR,5RS,6SR) ethyl 3-fluoro-2-oxobicyclo[3.1.0]hexane-6-carboxylate A solution of 6.60 g of (1SR,5RS,6SR)ethyl 2-oxobicyclo[3.1.0]hexane-6-carboxylate in 150 ml of tetrahydrofuran was added dropwise to a solution of lithium bis(trimethylsilyl)amide prepared by treatment of 7.50 g of 1,1,1,3,3,3-hexamethyl disilazane with 30.9 ml of n-butyl lithium (1.54 M hexane solution) in 150 ml of tetrahydrofuran, at −75° C. under a nitrogen atmosphere. After stirring for 1 hour at this temperature, 7.5 ml of chlorotrimethylsilane was added, and it was stirred for 1 hour at room temperature. After concentration of the reaction solution under reduced pressure, anhydrous hexane was added to the residue, the resulting inorganic salts were filtered off, and concentration was carried out.

The residue was dissolved in 66 ml of methylene chloride, and 15.00 g of N-fluorobenzenesulfonimide was added thereto, and it was stirred at room temperature for 16.5 hours. After washing the reaction solution twice with water, it was dried over anhydrous sodium sulfate, and after filtering off the desiccant, concentration was carried out under reduced pressure. The residue was purified by chromatography (silica gel: Wako gel (made by Wako Pure Chemical Industries Ltd.), eluent: hexane-methylene chloride-ethyl acetate=60:4:1), yielding 4.30 g of a mixture of (1SR,3RS,5RS,6SR)ethyl 3-fluoro-2-oxobicyclo[3.1.0]hexane-6-carboxylate and (1SR,3SR,5RS,6SR) ethyl 3-fluoro-2-oxobicyclo[3.1.0]hexane-6-carboxylate.

$^1$H-NMR(CDCl$_3$) δ (ppm); 1.28 (3H×3/4, t, J=7.2 Hz), 1.29 (3H×1/4, t, J=7.2 Hz), 2.11–2.79 (5H, m), 4.18 (2H, q, J=7.2 Hz), 4.51 (1H×1/4, dd, J=51 Hz, 8.1 Hz), 4.58 (1H×3/4, dt, J=51 Hz, 8.1 Hz)

MS(FAB) (Pos) m/e; 187 (M$^+$+1)

EXAMPLE 2

Syntheses of (1SR,3RS,5RS,6SR)ethyl 3-fluoro-2-oxobicyclo[3. 1.0]hexane-6-carboxylate and (1SR, 3SR,5RS,6SR)ethyl 3-fluoro-2-oxobicyclo[3.1.0]hexane-6-carboxylate A solution of 0.20 g of (1SR,5RS,6SR)ethyl 2-oxobicyclo[3.1.0]hexane-6-carboxylate in 6 ml of tetrahydrofuran was added dropwise to a solution of lithium bis(trimethylsilyl)amide prepared by treatment of 0.38g of 1,1,1,3,3,3-hexamethyldisilazane with 1.5 ml of n-butyl lithium (1.54 M hexane solution) in 6 ml of tetrahydrofuran, at −75° C. under a nitrogen atmosphere. After stirring for 45 minutes at this temperature, 0.75 g of N-fluorobenzenesulfonimide was added thereto, and it was stirred for 2 hours at room temperature. After washing the reaction solution twice with water, it was dried over anhydrous sodium sulfate, and after filtering off the desiccant, concentration was carried out under reduced pressure. The residue was purified by chromatography (silica gel: Wako gel (made by Wako Pure Chemical Industries Ltd.), eluent: hexane-methylene chloride-ethyl acetate =60:4:1), yielding 0.08 g of a mixture of (1SR,3RS,5RS,6SR)ethyl 3-fluoro-2-oxobicyclo[3.1.0]hexane-6-carboxylate and (1SR,3SR,5RS,6SR)ethyl 3-fluoro-2-oxobicyclo[3.1.0]hexane-6-carboxylate.

$^1$H-NMR(CDCl$_3$) δ (ppm); 1.28 (3H×3/4, t, J=7.2 Hz), 1.29 (3H×1/4, t, J=7.2 Hz), 2.11–2.79 (5H, m), 4.18 (2H, q, J=7.2 Hz), 4.51 (1H×1/4, dd, J=51 Hz, 8.1 Hz), 4.58 (1H×3/4, dt, J=51 Hz, 8.1 Hz)

MS(FAB) (Pos) m/e; 187 (M$^+$+1)

EXAMPLE 3

Synthesis of (1SR,5RS,6SR)ethyl 3,3-difluorobicyclo [3.1.0]hexane-6-carboxylate

A solution of 6.60 g of (1SR,5RS,6SR)ethyl 2-oxobicyclo[3.1.0]hexane-6-carboxylate in 150 ml of tetrahydrofuran was added dropwise to a solution of lithium bis (trimethylsilyl)amide prepared by treatment of 7.50 g of 1,1,1,3,3,3-hexamethyldisilazane with 30.9 ml of n-butyl lithium (1.54 M hexane solution) in 150 ml of tetrahydrofuran, at −75° C. under a nitrogen atmosphere. After stirring for 1 hour at this temperature, 7.5 ml of chlorotrimethylsilane was added thereto, and it was stirred for 1 hour at room temperature. After concentration of the reaction solution under reduced pressure, anhydrous hexane was added to the residue, the resulting inorganic salts were filtered off, and concentration was carried out. The residue was dissolved in 66 ml of methylene chloride, 15.00 g of N-fluorobenzenesulfonimide was added, and it was stirred at room temperature for 16.5 hours. After washing the reaction solution twice with water, it was dried over anhydrous sodium sulfate, and after filtering out the dessicant, concentration was carried out under reduced pressure. The residue was purified by chromatography (silica gel: Wako gel (made by Wako Pure Chemical Industries Ltd.), eluent: hexane-methylene chloride-ethyl acetate=60:4:1), yielding 0.02 g of (1SR,5RS,6SR)ethyl 3,3-difluorobicyclo[3.1.0]hexane-6-carboxylate.

$^1$H-NMR(CDCl$_3$) δ (ppm); 1.30 (3H, t, J=7.1Hz), 2.42–2.80 (5H, m), 4.20 (2H, q, J=7.1 Hz)

MS(Ion Spray) (Nega) m/e; 203 (M$^+$−1)

EXAMPLE 4

Synthesis of (1SR,5RS,6SR)ethyl 3,3-difluorobicyclo[3.1.0]hexane-6-carboxylate

A solution of 1.3 g of the compound synthesized in Example 1 dissolved in 6.5 ml of tetrahydrofuran was added dropwise to a solution of lithium bis (trimethylsilyl) amide prepared by treatment of 1.40 g of 1,1,1,3,3,3-hexamethyldisilazane with 5.0 ml of n-butyl lithium (1.54 M hexane solution) in 26 ml of tetrahydrofuran, at −75° C. under a nitrogen atmosphere. After stirring for 1 hour at this temperature, 1.3 ml of chlorotrimethylsilane was added thereto, and it was stirred for 1 hour at room temperature. After concentration of the reaction solution under reduced pressure, anhydrous hexane was added to the residue, the resulting inorganic salts were filtered off, and concentration was carried out.

The residue was dissolved in 13ml of methylene chloride, 3.30 g of N-fluoro benzenesulfonimide was added, and it was stirred at room temperature for 5 hours. After washing the reaction solution twice with water, it was dried over anhydrous sodium sulfate, and after filtering off the desiccant, concentration was carried out under reduced pressure. The residue was purified by chromatography (silica gel: Wako gel (made by Wako Pure Chemical Industries Ltd.), eluent: hexane-methylene chloride-ethyl acetate= 60:4:1), yielding 0.34 g of (1SR,5RS,6SR)ethyl 3,3-difluorobicyclo[3.1.0]hexane-6-carboxylate.

$^1$H-NMR(CDCl$_3$) δ (ppm); 1.30 (3H, t, J=7.1Hz), 2.42–2.80 (5H, m), 4.20 (2H, q, J=7.1 Hz)

MS(Ion Spray) (Nega) m/e; 203 (M$^+$−1)

EXAMPLE 5

Syntheses of (1SR,2SR,3SR,5RS,6SR)ethyl 2-spiro-5'-hydantoin-3-fluorobicyclo[3.1.0]hexane-6-carboxylate, (1SR,2SR,3RS,5SR,6SR)ethyl 2-spiro-5'-hydantoin-3-fluorobicyclo[3.1.0] hexane-6-carboxylate, and (1SR,2RS,3RS,5RS,6SR)ethyl 2-spiro-5'-hydantoin-3-fluorobicyclo[3.1.0]hexane-6-carboxylate To a solution of 4.84 g of a mixture of (1SR,3RS,5RS, 6SR)ethyl 3-fluoro-2-oxobicyclo[3.1.0]hexane-6-carboxylate and (1SR,3SR, 5RS, 6SR)ethyl 3-fluoro-2-oxobicyclo[3.1.0]hexane-6-carboxylate in a mixed solvent of 26 ml water and 38 ml ethanol were added 6.25 g of ammonium carbonate and 1.86 g of potassium cyanide, and then stirring was carried out for 37 hours at 35° C. After the reaction mixture was cooled to room temperature, 31 ml water was added, stirring was continued for further 2.5 hours with ice-cooling, and the resulting crystals were collected by filtration to yield 2.10 g of first crystals. With ice-cooling, concentrated hydrochloric acid was added to the filtrate to adjust its pH to 1.0, and the resulting crystals were collected by filtration to yield 2.00 g of second crystals.

The first crystals were submitted to chromatography (silica gel: Wako gel (made by Wako Pure Chemical Industries Ltd.), eluent: chloroform-methanol=100:1), separating them into 0.61 g of low-polarity diastereomer and 0.55 g of polar diastereomer A (including about 25% polar diastereomer B, with the same Rf value for polar diastereomer A and polar diastereomer B).

0.61 g of the low-polarity diastereomer was recrystallized from a mixed solvent of water-ethanol=1:1, yielding 0.52 g of (1SR,2SR,3SR,5RS,6SR)ethyl 2-spiro-5'-hydantoin-3-fluorobicyclo[3.1.0]hexane-6-carboxylate.

$^1$H-NMR(DMSO-d$_6$) δ (ppm); 1.19 (3H, t, J=7.0Hz), 1.95–2.46 (5H, m), 4.06 (2H, q, J=7.0 Hz), 4.81 (1H, dd, J=52 Hz, 5.1 Hz), 8.44 (1H, s), 10.91 (1H, s)

MS(EI) m/e; 256 (M$^+$)

Also, 0.55 g of the polar diastereomer A was recrystallized from a mixed solvent of water-ethanol=1:1, yielding 0.37 g of (1SR,2SR,3RS,5RS,6SR) ethyl 2-spiro-5'-hydantoin-3-fluorobicyclo[3.1.0]hexane-6-carboxylate.

$^1$H-NMR(DMSO-d$_6$) δ (ppm); 1.18 (3H, t, J=7.1 Hz), 1.85–2.43 (5H, m), 4.05 (2H, q, J=7.1 Hz), 4.70 (1H, dt, J=52 Hz, 8.0 Hz), 8.21 (1H, s), 10.83 (1H, s)

MS(EI) m/e; 256 (M$^+$)

The second crystals were washed with ethyl acetate, and after the insoluble matter was filtered off, the filtrate was concentrated under reduced pressure, and the residue was recrystallized twice from water-ethanol=1:1. This twice recrystallized filtrate was concentrated under reduced pressure, and the residue was submitted to chromatography (silica gel: Wako gel (made by Wako Pure Chemical Industries Ltd.), eluent: chloroform-methanol=100:1), completely removing the aforesaid low-polarity diastereomer. 0.25 g of crystals of the resulting polar diastereomer B (including about 10% polar diastereomer A) was recrystallized from water-ethanol =1:1, yielding 0.18 g of (1SR,2RS,3RS,5RS, 6SR)ethyl 2-spiro-5'-hydantoin-3-fluorobicyclo[3.1.0] hexane-6-carboxylate.

$^1$H-NMR(DMSO-d$_6$) δ (ppm); 1.18 (3H, t, J=7.1 Hz), 1.81–2.17 (4H, m), 2.36 (1H, dd, J=13 Hz, 7.2 Hz), 3.95–4.11 (2H, m), 4.90 (1H, ddd, J=51 Hz, 8.9 Hz, 7.2 Hz), 8.54 (1H, s), 10.87 (1H, s)

MS(EI) m/e; 256 (M$^+$)

Also, the following compound was synthesized in the same way as above.

(1SR,2SR,5RS,6SR)ethyl 2-spiro-5'-hydantoin-3,3-difluorobicyclo[3.1.0]hexane-6-carboxylate $^1$H-NMR(DMSO-d$_6$) δ (ppm); 1.19 (3H, t, J=7.0 Hz), 1.85–1.89 (1H, m), 2.00–2.08 (1H, m), 2.15–2.27 (1H, m), 2.33–2.50 (1H, m), 2.55–2.86 (1H, m), 4.07 (2H, q, J=7.0 Hz), 8.49 (1H, m)

MS(EI) m/e; 274 (M$^+$)

EXAMPLE 6

Synthesis of (1SR,2SR,3RS,5RS,6SR)-2-amino-3-fluorobicyclo[3.1.0]hexane-2,6-dicarboxylic acid 300 mg of (1SR,2SR,3RS,5RS,6SR)ethyl 2-spiro-5'-hydantoin-3-fluorobicyclo[3.1.0]hexane-6-carboxylate was dissolved in 2.5 ml of aqueous 3 M sodium hydroxide solution, and heated under reflux for 16 hours. After the reaction solution was cooled to room temperature, it was filtered with a glass filter, and after the filtrate was brought to pH 3 with concentrated hydrochloric acid, it was purified by ion exchange chromatography (AG1-X8 anion exchange resin (Bio-Rad), eluent: 0.1 M acetic acid to 3 M acetic acid), yielding 51 mg of (1SR,2SR,3RS,5RS,6SR)-2-amino-3-fluorobicyclo[3.1.0]hexane-2,6-dicarboxylic acid.

$^1$H-NMR(TFA-d) δ (ppm); 2.23–2.24 (1H, m), 2.56–2.96 (4H, m), 5.15 (1H, dt, J=52 Hz, 7.5 Hz)

MS(CI) m/e; 204 (M$^+$+1)

Also, the following compound was synthesized in the same way as above.

(1SR,2SR,5RS,6SR)-2-amino-3,3-difluorobicyclo[3.1.0]hexane-2,6-dicarboxylic acid $^1$H-NMR(TFA-d) δ (ppm); 2.46 (1H, brs), 2.63–2.90(3H, m), 3.01–3.12 (1H, m)

MS(CI) m/e; 222 (M$^+$+1)

EXAMPLE 7

Synthesis of (1SR,2SR,3SR,5RS,6SR)-2-amino-3-fluorobicyclo[3.1.0]hexane-2,6-dicarboxylic acid 100 mg of (1SR,2SR,3SR,5RS,6SR)ethyl 2-spiro-5'-hydantoin-3-fluorobicyclo[3.1.0]hexane-6-carboxylate was dissolved in 1.5 ml of aqueous 60% sulfuric acid, and heated at 140° C. for 12 hours. After the reaction solution was cooled to room temperature, it was brought to pH 8 with an aqueous 5 M sodium hydroxide, then it was purified by ion exchange chromatography (AG1-X8 anion exchange resin (Bio-Rad), eluent: 0.1 M acetic acid to 2 M acetic acid), yielding 20 mg of (1SR,2SR,3SR,5RS,6SR) -2-amino-3-fluorobicyclo[3.1.0]hexane-2,6-dicarboxylic acid.

$^1$H-NMR(TFA-d) δ (ppm); 2.49 (1H, brs), 2.59–3.06(4H, m), 5.40 (1H, dd, J=52 Hz, 5.3 Hz)

MS(CI) m/e; 204 (M$^+$+1)

Also, the following compound was synthesized in the same way as above.

(1SR,2RS,3RS,5RS,6SR)-2-amino-3-fluorobicyclo[3.1.0]hexane-2,6-dicarboxylic acid $^1$H-NMR(TFA-d) δ (ppm); 2.33 (1H, brs), 2.54–2.89(4H, m), 5.42–5.59 (1H, m)

MS(CI) m/e; 204(M$^+$+1)

EXAMPLE 8

Synthesis of (1S,2S,3S,5R,6S)-2-amino-3-fluorobicyclo[3.1.0]hexane-2,6-dicarboxylic acid (1) A mixture of 2.20 g of (1SR,2SR,3SR,5RS,6SR)ethyl 2-spiro-5'-hydantoin-3-fluorobicyclo[3.1.0]hexane-6-carboxylate and 17 ml of aqueous 2 M sodium hydroxide was stirred at room temperature. After 2 hours, its pH was adjusted to 1.0 by adding concentrated hydrochloric acid. The resulting crystals were isolated by filtration, yielding 1.81 g of (1SR,2SR,3SR,5RS,6SR)-2-spiro-5'-hydantoin-3-fluorobicyclo[3.1.0]hexane-6-carboxylic acid.

$^1$H-NMR(DMSO-d$_6$) δ (ppm); 1.85–2.44 (5H, m), 4.80 (1H, dd, J=52 Hz, 5.3 Hz), 8.44 (1H, s), 10.88 (1H, s), 12.30 (1H, brs)

MS(FAB) (Nega) m/e; 227 (M$^+$1)

(2) 1.80 g of (1SR,2SR,3SR,5RS,6SR)-2-spiro-5'-hydantoin -3-fluorobicyclo[3.1.0]hexane-6-carboxylic acid was stirred at 55° C. in 26 ml of a mixed solution of acetone:water=8:5, and after adding 0.96 g of (R)-(+)-1-phenylethylamine, it was stirred for 15 hours at room temperature. The resulting crystals were filtered, yielding 1.30 g of (R)-(+)-1-phenylethylamine salt. Also, the filtrate was used in Example 9.

Next, to a suspension of 1.20 g of this salt in 15ml of water, 1 M hydrochloric acid was added for adjusting the pH to 1.0, and it was stirred at room temperature for 14 hours. The resulting crystals were isolated by filtration, yielding 0.65 g of (1S,2S,3S,5R,6S)-2-spiro-5'-hydantoin-3-fluorobicyclo[3.1.0]hexane-6-carboxylic acid. The filtrate was further purified by ion exchange chromatography (AG50W-X8 cation exchange resin (Bio-Rad), eluent: 1 M acetic acid), yielding 0.06 g of (1S,2S,5R,6S)-2-spiro-5'-hydantoin-3-fluorobicyclo[3.1.0]hexane-6-carboxylic acid.

$^{22}$[α]$_D$=+36.84 (c=0.20, MeOH)

(3) 0.60g of (1S,2S,3S,5R,6S)-2-spiro-5'-hydantoin-3-fluorobicyclo[3.1.0]hexane-6-carboxylic acid was dissolved in 10 ml of aqueous 60% sulfuric acid, and it was stirred at 140° C. for 2 days. The reaction solution, after cooling to room temperature, was brought to pH 8 by addition of aqueous 5 M sodium hydroxide, then it was purified with ion exchange chromatography (AG1-X8 anion exchange resin (Bio-Rad), eluent: 0.1 M acetic acid to 2 M acetic acid), yielding 0.34 g of (1S,2S,3S,5R,6S)-2-amino-3-fluorobicyclo[3.1.0]hexane-2,6-dicarboxylic acid.

$^{22}$[α]$_D$=+58.61 (c=0.20, 1 N HCl)

EXAMPLE 9

Synthesis of (1R,2R,3R,5S,6R)-2-amino-3-fluorobicyclo[3.1.0]hexane-2,6-dicarboxylic acid (1) The filtrate of Example 8 (2) was concentrated under reduced pressure. A mixture of 1.3 g of the resulting crystals and 17 ml of water was adjusted to a pH of 1.0 by addition of 1 M hydrochloric acid and was stirred at room temperature. After 4 hours, the resulting crystals were collected by filtration, yielding 0.81 g of crystals. The filtrate was purified by ion exchange chromatography (AG50W-X8 cation exchange resin (Bio-Rad), eluent: 1 M acetic acid)., yielding 0.08 g of crystals.

(2) The above two crystals were combined (0.89 g), 13 ml of a mixed solution of acetone:water=8:5 was added, and stirring was carried out at 55° C. 0.47 g of (S)-(−)-1-phenylethylamine was added to this solution, and it was stirred at room temperature for 15 hours. The resulting crystals were filtered, yielding 1.10 g of (R)-(−)-1-phenylethylamine salt.

This salt was made into a free form by treatment with 1 M hydrochloric acid in the same way as in (2) of Example 8, yielding 0.58 g of (1R,2R,3R,5S,6R)-2-spiro-5'-hydantoin-3-fluorobicyclo[3.1.0]hexane-6-carboxylic acid. The filtrate was purified by ion exchange chromatography (AG50W-X8 cation exchange resin (Bio-Rad), eluent: 1 M acetic acid), yielding 0.07 g of (1R,2R,3R,5S,6R)-2-spiro-5'-hydantoin-3-fluorobicyclo[3.1.0]hexane-6-carboxylic acid.

$^{22}$[α]$_D$=−37.52 (c=0.20, MeOH)

(3) 0.58 g of (1R,2R,3R,5S,6R)-2-spiro-5'-hydantoin-3-fluorobicyclo[3.1.0]hexane-6-carboxylic acid was reacted as in (3) of Example 8, yielding 0.37 g of (1R,2R,3R,5S,6R)-2-amino-3-fluorobicyclo[3.1.0]hexane-2,6-dicarboxylic acid.

$^{22}[\alpha]_D = -59.36$ (c=0.20, 1 N HCl)

Experimental Example 1
(Effect of Test Compound on cAMP Accumulation)

CHO cells stably expressing metabotropic glutamate receptors mGluR2 were seeded in a 96-well plate (1.26×104 cells/well/0.32 cm$^2$/150 µl) in Dalbecco-modified Eagle medium [1% proline 50 units/ml, penicillin 50 µg/ml, streptomycin 2 mM, L-glutamine (added when used)] containing 10% dialyzed fetal horse serum, and were cultured for 2 days at 37° C. under an atmosphere of 5% $CO_2$. After the medium was replaced with an L-glutamine free medium, they were cultured for 4 hours, and the supernatant liquid was aspirated. After adding 150 µl of PBS(+)-IBMX (10 mM PBS(-), 1 mM $MgCl_2$, 1 mM $CaClL_2$, 1 mM IBMX), incubation was conducted at 37° C. under the presence of 5% $CO_2$ for 20 minutes. Once again the supernatant liquid was suctioned off, 60 µl of 10-5 M Forskolin and PBS(+)-IBMX containing the specimens listed in Table 1 between 10-10 and 10-4 M were added, incubation was carried out for 15 minutes at 37° C. under the presence of 5% $CO_2$, and a study was made for the inhibitory effect of the antagonists on the Forskolin stimulation cAMP accumulation quantity [for control, the conditions were set to Forskolin with no addition of compounds (Tanabe et al., Neuron, 8, 169–179 (1992))]. The reactions were halted by adding 100 µl of ice-cold ethanol, the entire quantity of the supernatant liquid was collected in a separate plate, then was dried up at normal temperature with an evaporator, and was kept at −20° C. In the dried-up samples, the quantity of cAMP was measured using a cAMP EIA kit (from the Amasham company). The control value was subtracted from each cAMP quantity. The concentration value $ED_{50}$ of the concentration-of the test compound at which the CAMP accumulation was inhibited 50% when stimulation was effected by 10-5 M Forskolin was determined. The results are presented in Table 1.

TABLE 1

| Test compound | $ED_{50}$(nM) |
|---|---|
| Comp. 1 | 23.65 |
| Comp. 2 | 53.54 |
| LY354740 | 18.74 |
| Glutamate | 8770 |
| DCG IV | 98.28 |
| (1S,3R)-ACPD | 1500 |
| L-CCG-I | 121.04 |

Comp. 1: (1S, 2S, 3S, 5R, 6S)-2-amino-3-fluorobicyclo[3.1.0]hexane-2,6-dicarboxylic acid
Comp. 2: (1SR, 2SR, 3SR, 5RS, 6SR)-2-amino-3-fluorobicyclo [3.1.0]hexane-2,6-dicarboxylic acid
LY354740: (+) - (1S, 2S, 5R, 6S)-2-aminobicyclo[3.1.0]hexane-2,6-dicarboxylic acid
DCG IV: (2S, 2'R, 3'R)-2-(2', 3'-dicarboxycyclopropyl) glycine
(1S,3R) ACPD: (1S, 3R)-1-aninocyclopentane-1,3-dicarboxylic acid
L-CCG-I: (2S, 1'S, 2'S)-2-(carboxycyclopropyl) glycine Experimental Example 2
(Effect on Methamphetamine-induced Hyperactivity in Mice)

11–12 male ICR-strain mice (body weights 23–32 g, Charles River Japan Inc.) were used for a group. The mice were housed in a transparent cylindrical measurement cage made of vinyl chloride (diameter 30 cm, height 30 cm) and were acclimated to their environment for 90 minutes.

Next, each of the compounds listed in Table 2 was orally administered to the mice, and 30 minutes later, 1 mg/kg methamphetamine was administered intracelially. 15 minutes later, the 30-minute quantity of movement of the mice was measured by a count, using an automatic movement measurement device (SCANET/SV-10, from Toyo Sangyo Co., Ltd.). Each listed compound was used suspended in a solvent consisting of 0.3% Tween 80 physiological saline solution.

The inhibition rate was determined from the count of the group of mice given solvent only and the count of the group of mice given each prescribed dosage of the compounds listed in Table 2, and the $ED_{50}$ value was calculated. The results are given in Table 2. Statistical processing was done by analysis of variance (ANOVA), followed by Dunnet's test.

As shown in Table 2, except for the group to which 0.01 mg/kg, LY354740 was orally administered, as a comparison example, the methamphetamine-induced hyperactivity was inhibited in a dose-dependent manner [F(4,54)=3.242, P<0.05]. The $ED_{50}$ value was 0.87 mg/kg. A similar effect is also seen for Comp. 1, which is a compound according to this invention [F(3,43)=3.306, P<0.05]. However, the $ED_{50}$ value for the compound according to this invention was 0.05 mg/kg, showing 17.4 times the inhibition effect of LY354740 as for the methamphetamine-induced hyperactivity.

TABLE 2

| Compound | Dosage (mg/kg, p.o.) | N | Count | Inhibition rate (%) | $ED_{50}$ (mg/kg) |
|---|---|---|---|---|---|
| Comp. 1 | Vehicle | 11 | 11823 ± 3135 | | |
| | 0.01 | 12 | 9512 ± 3005 | 19.6 | 0.05 |
| | 0.1 | 12 | 4291 ± 1283* | 63.7 | |
| | 1 | 12 | 2353 ± 733* | 80.1 | |
| LY354740 | Vehicle | 12 | 10101 ± 2133 | | |
| | 0.01 | 11 | 12000 ± 3216 | −18.8 | 0.87 |
| | 0.1 | 12 | 6975 ± 1489 | 30.9 | |
| | 1 | 12 | 4534 ± 1116 | 55.1 | |
| | 10 | 12 | 3704 ± 1285 | 63.3 | |

N: Number of animals in one group.
*P < 0.01 comparison with group given the solvent
Comp. 1: (1S, 2S, 3S, 5R, 6S)-2-amino-3-fluorobicyclo[3.1.0]hexane-2,6-dicarboxylic acid
LY354740: (+)-(1S,2S,5R,6S)-2-aminobicyclo[3.1.0]hexane-2,6-dicarboxylic acid

INDUSTRIAL APPLICABILITY

The fluorine-containing amino acid derivatives of this invention are useful as drugs; in particular, they are useful as drugs that act upon metabotropic glutamate receptors. Therefore, this invention can be used for the treatment and prevention of psychiatric disorders such as, for example, schizophrenia, anxiety and associated diseases, depression, bipolar disorder, and epilepsy, as well as neurological diseases such as, for example, chemical dependence, cognitive disorders, Alzheimer's disease, Huntington's chorea, Parkinson's disease, movement impairment associated with muscular stiffness, cerebral ischemia, cerebral insufficiency, spinal cord lesions, and head trauma.

What is claimed is:
1. A fluorine-containing amino acid derivative represented by the formula

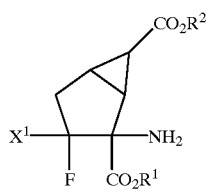

[where $X^1$ represents a hydrogen atom or a fluorine atom, and $R^1$ and $R^2$ are the same or different and each represents a hydrogen atom or an alkyl group of 1–10 carbon atoms], a pharmaceutically permissible salt thereof, or a hydrate thereof.

2. A fluorine-containing amino acid derivative having relative stereochemical arrangements represented by the formula

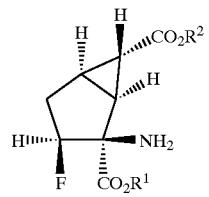

[where $R^1$ and $R^2$ are the same or different and each represents a hydrogen atom or an alkyl group of 1–10 carbon atoms], pharmaceutically permissible salts thereof, or hydrates thereof.

3. (1S,2S,3S,5R,6S)-2-amino-3-fluorobicyclo[3.1.0] hexane-2,6-dicarboxylic acid, a pharmaceutically permissible salt thereof, or a hydrate thereof.

4. A pharmaceutical preparation that contains the compound according to any one of claims 1–3, and one or more members selected from a pharmaceutically permissible carrier, filler, and diluent.

5. A drug which contains the compound according to any one of claims 1–3 as an active ingredient.

6. The drug according to claim 5 that is group 2 metabotropic glutamate receptor agonist.

7. A method of psychiatric therapy comprising administering an effective amount of a compound according to any one of claims 1–3 to a patient in need of the same.

8. A method of psychiatric therapy comprising administering an effective amount of a compound according to any one of claims 1–3 as a group 2 metabotropic glutamate receptor agonist to a patient in need of the same.

* * * * *